United States Patent [19]

Feldbau

[11] 4,350,154

[45] Sep. 21, 1982

[54] TEETH PROTECTING DEVICE

[76] Inventor: Elliot V. Feldbau, 53 South St., Natick, Mass. 01760

[21] Appl. No.: 254,970

[22] Filed: Apr. 16, 1981

[51] Int. Cl.³ .............................................. A61F 5/56
[52] U.S. Cl. .................................... 128/136; 433/37
[58] Field of Search .............. 433/6, 41, 47; 128/136

[56] References Cited

U.S. PATENT DOCUMENTS

| | | | |
|---|---|---|---|
| 1,489,192 | 4/1924 | Cleveland | 433/47 |
| 3,319,626 | 5/1967 | Lindsay | 433/6 |
| 3,457,916 | 7/1969 | Wolicki | 128/136 |
| 3,878,610 | 4/1975 | Coscina | 433/37 |

*Primary Examiner*—Robert Peshock
*Attorney, Agent, or Firm*—Robert T. Gammons

[57] ABSTRACT

A teeth-protecting device structured to cling to the teeth with sufficient tenacity to remain secure throughout oral exploration and/or corrective measures and yet to be removable without dislodging pre-existing dental repair work and/or weakly anchored teeth.

6 Claims, 5 Drawing Figures

TEETH PROTECTING DEVICE

BACKGROUND OF INVENTION

The provision of mouth-protecting and/or teeth-protecting devices for dental, medical and athletic purposes are shown in the United States patents listed below wherein an arcuate channel of U-shaped cross section is filled or partially filled with a matrix material for application to the teeth. The matrix material is designed to receive an impression of the teeth and to hold the channel in place. The principal objection to the structure shown in these patents resides in the fact that when the structure is removed, the matrix clings to the teeth with such tenacity that repairs such as fillings, bridgework and the like are loosened or pulled free and weak or loose teeth may be pulled out. It is the purpose of this invention to provide a tooth protecting device which will obviate these difficulties and to a method of protecting teeth during exploration and/or corrective procedures which will not adversely affect pre-existing dental work.

| | |
|---|---|
| 2,705,492 | Chandler |
| 3,016,052 | Zubren |
| 3,124,129 | Greenberg |
| 3,236,235 | Jacobs |
| 3,513,838 | Foderick et al |
| 3,864,832 | Carlson |

SUMMARY OF INVENTION

As herein illustrated, the teeth-protecting device comprises in combination an arcuate channel member of U-shaped cross section defined by a bottom wall and upstanding spaced side walls comprising an inner side wall and an outer side wall and a matrix composition of impressionable self-curing to rubber-like consistency, capable of conforming to the interior of the channel member and of receiving the impression of the teeth prior to curing and of lightly adhering to both the channel member and the teeth following curing, said channel being separable from the cured filling by peeling to leave the matrix intact and the matrix, in turn, being peelable from the teeth. The channel member is comprised of a rigid yet flexible material which can be flexed to disengage it from the matrix and in one form the front wall of the channel member contains arcuately-spaced, vertically-positioned lines of weakness dividing it into sections which enable breaking the front wall section-by-section away from the matrix. Desirably, the front wall of the channel contains arcuately-spaced, vertically-positioned slots which enable peeling the portions of the wall between the slots away from the matrix. After peeling the channel member away from the matrix, the matrix, in turn, may be peeled away from the teeth. The inner side of one of the walls of the channel members is desirably undercut and preferably it is the inner side of the front wall. The front wall is higher than the rear wall and the channel is open at both ends.

In accordance with the method of protecting teeth, a teeth-protecting device in the form of an arcuate, channel-shaped member of U-shaped cross section defined by a bottom wall and upstanding side walls filled with the matrix of impressionable material capable of curing to a rubber-like consistency is applied to the teeth, the matrix allowed to cure to hold the device in place during treatment and, after treatment, the device is removed by peeling the channel member from the matrix and the matrix from the teeth.

The invention will now be described in greater detail with reference to the accompanying drawings, wherein.

Figure 1:
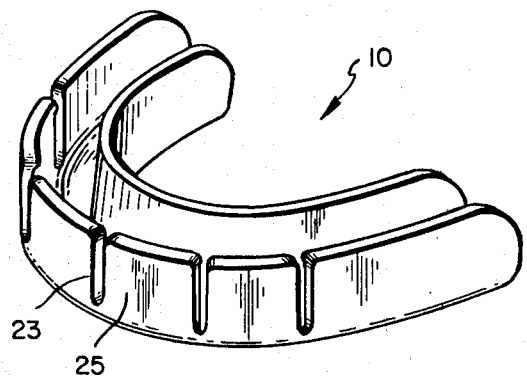
FIG. 1 is a perspective view of the teeth-protecting device of this invention with the matrix omitted and showing slots in the front wall.
Figure 2:
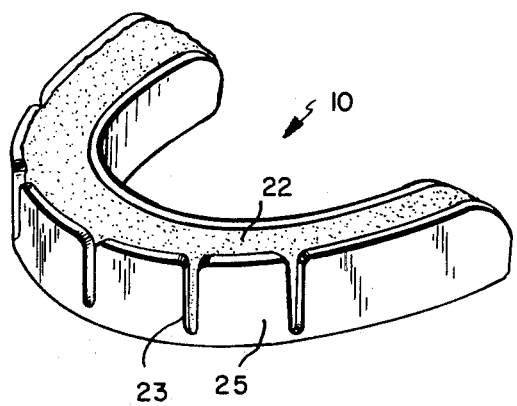
FIG. 2 is a perspective view like FIG. 1 with the matrix included.
Figure 3:
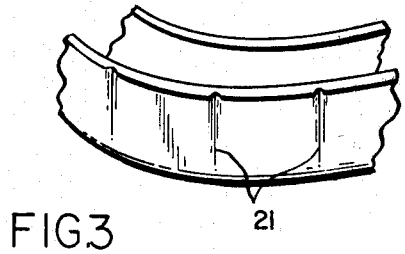
FIG. 3 is a fragmentary view of the device showing lines of weakness in the front wall.
Figure 4:
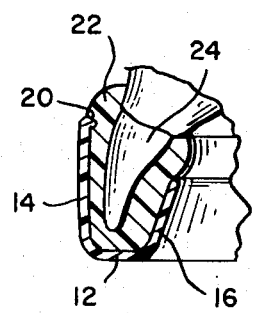
FIG. 4 is a section showing the device applied to the teeth.

Referring to the drawings, the teeth-protecting device 10 of this invention is an arcuate channel-shaped member of U-shaped cross section throughout its arcuate length. The channel-shaped member is defined by a bottom wall 12, a front side wall 14 and a rear side wall 16. The ends of the channel-shaped member defined by the bottom and side walls are open and, preferably, the inner side of the front wall is provided with an undercut or shoulder 20.

Within the channel-shaped member and functioning in combination with the channel-shaped member is a matrix material 22 capable of receiving the indentation of the teeth 24 to which the device is applied for protection, capable of curing to a rubber-like consistency and capable of clinging both to the channel-shaped member and to the teeth with sufficient intensity to retain the channel-shaped member and to retain the teeth during normal exploratory and/or corrective measures carried out by dental or medical practitioners.

Figure 5:
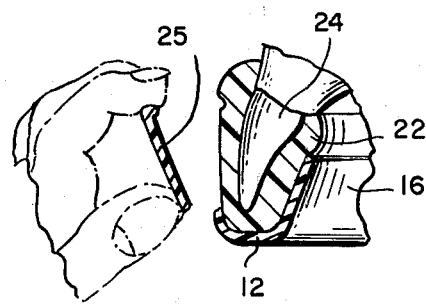
FIG. 5 illustrates the first step in removing the device from the matrix section-by-section.

An important aspect of this invention which distinguishes it from the aforesaid prior art is to use a matrix which will receive the impression of the teeth without having to elevate its temperature to an uncomfortable degree and/or to employ solvents which are disagreeable, which will set up or cure at mouth temperature without becoming uncomfortably rigid and which will cling both to the channel-shaped member within which it is contained and to the teeth contained therein with sufficient tenacity to remain in place, but, at the same time, can be removed without loosening pre-existing dental work and without loosening or pulling out weak or loose teeth. This is achieved in part by using a dental impression compound comprised of dimethylsiloxane-type dental compound which is elastomeric and resilient. Further, in accordance with the invention, the channel-shaped member is made of a molded plastic which, while rigid, is sufficiently flexible so as to enable peeling it away from the matrix without applying a pull upon the matrix itself which would tend to loosen pre-existing dental work or pull loose already loose teeth. To facilitate the peeling away of the channel-shaped member, the latter may be provided with arcuately-spaced, vertically-positioned lines of weakness 21 or slots 23 so that the portions 25 between the lines of weakness or slots can broken away from each other and peeled one-by-one away from the matrix without, at the same time, applying a pulling force on the matrix itself which might dislodge dental work or teeth. FIG. 5 diagrammatically illustrates detaching portions 25 section-by-section so as to expose the matrix. After the portions 25 have been detached, it is easy to peel the remainder of the channel member away from the lower part of the matrix and, after this, to peel the matrix itself away from the teeth.

The device as thus described serves a very important improvement in the art over the prior art as described in the patents listed above which are unacceptable for the several reasons enumerated, to wit, that some require heating the matrix to a temperature which is manifestly undesirable from the standpoint of the patient, others require unacceptably long periods for setting up to a condition such as to retain the impression of the teeth and so to remain in place, still others of which set up to a hardness which is not only uncomfortable for the patient, but detrimental, and all of which so cling to the teeth that removal loosens and/or pulls out pre-existing dental work and loose or weak teeth.

It should be understood that the present disclosure is for the purpose of illustration only and includes all modifications or improvements which fall within the scope of the appended claims.

What is claimed is:

1. A teeth-protecting device comprising in combination an arcuate channel member of U-shaped cross section defined by a bottom wall and upstanding, spaced side walls comprising an inner side wall and an outer side wall, and a matrix comprising an impressionable, self-curing to a rubber-like consistency material, capable of conforming to the interior of the channel member and of receiving the impression of the teeth prior to curing and of lightly adhering to both the channel member and the teeth following curing, and wherein the outer side wall of the channel member contains arcuately-spaced, vertically-positioned slots which enable peeling the portion of the outer side wall between longitudinal slots away from the matrix to leave the matrix intact and the matrix, in turn, being peelable from the teeth.

2. A teeth-protecting device according to claim 1 wherein the inner side of one of the walls is undercut.

3. A teeth-protecting device according to claim 1 wherein the inner side of the front wall is undercut.

4. A teeth-protecting device according to claim 1 wherein the front wall is higher than the rear wall.

5. A teeth-protecting device according to claim 1 wherein the channel is open at both ends.

6. The method of protecting teeth during oral exploration and/or corrective treatment comprising applying a teeth protector in the form of an arcuate channel-shaped member of U-shaped cross section defined by a bottom wall and upstanding, spaced, side walls comprising a front wall and a back wall within which is deposited a matrix of impressionable material capable of curing to a rubber-like consistency, to the teeth to cause the teeth to become indented in the matrix, allowing the matrix to set to hold the teeth protector in place during treatment and, following such treatment, removing the teeth protector by peeling the portions of the between the slots, one by one away from the matrix and thereafter peeling the matrix from the teeth.

* * * * *